(12) United States Patent
Zhukovsky et al.

(10) Patent No.: US 11,958,913 B2
(45) Date of Patent: *Apr. 16, 2024

(54) POLYPEPTIDE LINKER FOR PREPARING MULTISPECIFIC ANTIBODIES

(71) Applicant: BIOMUNEX PHARMACEUTICALS, Paris (FR)

(72) Inventors: Eugene Zhukovsky, Bethel, CT (US); Olivier Leger, Saint Sixt (FR)

(73) Assignee: BIOMUNEX PHARMACEUTICALS, Paris (FR)

( * ) Notice: Subject to any disclaimer, the term of this patent is extended or adjusted under 35 U.S.C. 154(b) by 489 days.

This patent is subject to a terminal disclaimer.

(21) Appl. No.: 16/476,624

(22) PCT Filed: Jan. 9, 2018

(86) PCT No.: PCT/EP2018/050481
§ 371 (c)(1),
(2) Date: Jul. 9, 2019

(87) PCT Pub. No.: WO2018/127608
PCT Pub. Date: Jul. 12, 2018

(65) Prior Publication Data
US 2019/0330377 A1    Oct. 31, 2019

(30) Foreign Application Priority Data
Jan. 9, 2017    (EP) .................................... 17305022

(51) Int. Cl.
| C07K 16/04 | (2006.01) |
| A61K 47/68 | (2017.01) |
| C07K 16/28 | (2006.01) |
| C07K 16/32 | (2006.01) |
| C07K 16/46 | (2006.01) |

(52) U.S. Cl.
CPC ........ C07K 16/468 (2013.01); C07K 16/2827 (2013.01); C07K 16/2863 (2013.01); C07K 16/2896 (2013.01); C07K 16/32 (2013.01); C07K 2317/14 (2013.01); C07K 2317/24 (2013.01); C07K 2317/31 (2013.01); C07K 2317/41 (2013.01); C07K 2317/522 (2013.01); C07K 2317/524 (2013.01); C07K 2317/526 (2013.01); C07K 2317/53 (2013.01); C07K 2317/55 (2013.01)

(58) Field of Classification Search
CPC ........ C07K 16/04; C07K 16/28; C07K 16/32; A61K 47/68
USPC ........................................................ 424/133.1
See application file for complete search history.

(56) References Cited

U.S. PATENT DOCUMENTS

| 2019/0153104 A1 | 5/2019 | Zhukovsky et al. | |
| 2019/0330377 A1* | 10/2019 | Zhukovsky | ........ C07K 16/2896 |
| 2020/0010559 A1 | 1/2020 | Zhukovsky et al. | |
| 2020/0299413 A1 | 9/2020 | Zhukovsky et al. | |

FOREIGN PATENT DOCUMENTS

| WO | WO 2012/088461 | 6/2012 |
| WO | WO 2013/005194 | 1/2013 |
| WO | WO 2017/162890 | 9/2017 |
| WO | WO 2017/186950 | 11/2017 |
| WO | WO 2018/178101 | 10/2018 |

OTHER PUBLICATIONS

Chen et al. (Adv Drug Deliv Rev. Oct. 15, 2013; 65(10): 1357-1369).*
Reusch et al (MAbs. May-Jun. 2015; 7(3): 584-604).*
Golay, J. et al. "Design and Validation of a Novel Generic Platform for the Production of Tetravalent IgG1-like Bispecific Antibodies" *The Journal of Immunology*, Apr. 1, 2016, pp. 3199-3211, vol. 196, No. 7, supplemental p. 1.
Written Opinion in International Application No. PCT/EP2018/050481, dated Mar. 26, 2018, pp. 1-10.
Claims pending in U.S. Appl. No. 16/088,181, filed Sep. 25, 2018, pp. 1-3.

* cited by examiner

*Primary Examiner* — Lynn A Bristol
(74) *Attorney, Agent, or Firm* — Saliwanchik, Lloyd & Eisenschenk

(57) ABSTRACT

The present invention relates to a mutant polypeptide linker for preparing multispecific antibodies, multispecific antibodies, and methods for producing multispecific antibodies.

12 Claims, 6 Drawing Sheets
Specification includes a Sequence Listing.

SEQUENCE LISTING

```
<160> NUMBER OF SEQ ID NOS: 23

<210> SEQ ID NO 1
<211> LENGTH: 34
<212> TYPE: PRT
<213> ORGANISM: Artificial Sequence
<220> FEATURE:
<223> OTHER INFORMATION: linker
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
```

```
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 1

Glu Pro Lys Xaa Cys Asp Lys Xaa His Xaa Xaa Pro Pro Xaa Pro Ala
1               5                   10                  15

Pro Glu Leu Leu Gly Gly Pro Xaa Xaa Pro Pro Xaa Pro Xaa Pro Xaa
                20                  25                  30

Gly Gly

<210> SEQ ID NO 2
<211> LENGTH: 34
<212> TYPE: PRT
<213> ORGANISM: Artificial Sequence
<220> FEATURE:
<223> OTHER INFORMATION: linker

<400> SEQUENCE: 2

Glu Pro Lys Ser Cys Asp Lys Thr His Thr Ser Pro Pro Ala Pro Ala
1               5                   10                  15

Pro Glu Leu Leu Gly Gly Pro Gly Gly Pro Pro Gly Pro Gly Pro Gly
                20                  25                  30

Gly Gly

<210> SEQ ID NO 3
<211> LENGTH: 34
<212> TYPE: PRT
<213> ORGANISM: Artificial Sequence
<220> FEATURE:
<223> OTHER INFORMATION: linker

<400> SEQUENCE: 3

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Ala Pro Ala Pro Ala
                20                  25                  30

Gly Gly

<210> SEQ ID NO 4
<211> LENGTH: 34
<212> TYPE: PRT
<213> ORGANISM: Artificial Sequence
<220> FEATURE:
<223> OTHER INFORMATION: linker

<400> SEQUENCE: 4

Glu Pro Lys Ser Cys Asp Lys Thr His Thr Ser Pro Pro Ala Pro Ala
1               5                   10                  15

Pro Glu Leu Leu Gly Gly Pro Ala Ala Pro Pro Gly Pro Ala Pro Gly
                20                  25                  30

Gly Gly

<210> SEQ ID NO 5
<211> LENGTH: 34
<212> TYPE: PRT
<213> ORGANISM: Artificial Sequence
<220> FEATURE:
```

<223> OTHER INFORMATION: linker

<400> SEQUENCE: 5

Glu Pro Lys Ser Cys Asp Lys Thr His Thr Cys Pro Pro Cys Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 6
<211> LENGTH: 34
<212> TYPE: PRT
<213> ORGANISM: Artificial Sequence
<220> FEATURE:
<223> OTHER INFORMATION: linker

<400> SEQUENCE: 6

Glu Pro Lys Ser Cys Asp Lys Thr His Thr Ser Pro Pro Ser Pro Ala
1               5                   10                  15

Pro Glu Leu Leu Gly Gly Pro Ser Thr Pro Pro Thr Pro Ser Pro Ser
            20                  25                  30

Gly Gly

<210> SEQ ID NO 7
<211> LENGTH: 120
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 8
<211> LENGTH: 98
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 9
<211> LENGTH: 119
<212> TYPE: PRT
<213> ORGANISM: Homo sapiens

<400> SEQUENCE: 9

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala
        115

<210> SEQ ID NO 10
<211> LENGTH: 98
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Glu Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 11
<211> LENGTH: 15
<212> TYPE: PRT
<213> ORGANISM: Homo sapiens

<400> SEQUENCE: 11
```

```
Glu Pro Lys Ser Cys Asp Lys Thr His Thr Cys Pro Pro Cys Pro
1               5                   10                  15
```

<210> SEQ ID NO 12
<211> LENGTH: 110
<212> TYPE: PRT
<213> ORGANISM: Homo sapiens

<400> SEQUENCE: 12

```
Ala Pro Glu Leu Leu Gly Gly Pro Ser Val Phe Leu Phe Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 13
<211> LENGTH: 107
<212> TYPE: PRT
<213> ORGANISM: Homo sapiens

<400> SEQUENCE: 13

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 14
<211> LENGTH: 701
<212> TYPE: PRT
<213> ORGANISM: Homo sapiens

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
```

```
            50                  55                  60
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Ser Pro Pro Ala Pro Ala Pro Glu Leu Leu Gly Gly
225                 230                 235                 240

Pro Gly Gly Pro Pro Gly Pro Gly Pro Gly Gly Gln Val Gln Leu
            245                 250                 255

Lys Gln Ser Gly Pro Gly Leu Val Gln Pro Ser Gln Ser Leu Ser Ile
                260                 265                 270

Thr Cys Thr Val Ser Gly Phe Ser Leu Thr Asn Tyr Gly Val His Trp
                275                 280                 285

Val Arg Gln Ser Pro Gly Lys Gly Leu Glu Trp Leu Gly Val Ile Trp
            290                 295                 300

Ser Gly Gly Asn Thr Asp Tyr Asn Thr Pro Phe Thr Ser Arg Leu Ser
305                 310                 315                 320

Ile Asn Lys Asp Asn Ser Lys Ser Gln Val Phe Phe Lys Met Asn Ser
                325                 330                 335

Leu Gln Ser Asn Asp Thr Ala Ile Tyr Tyr Cys Ala Arg Ala Leu Thr
                340                 345                 350

Tyr Tyr Asp Tyr Glu Phe Ala Tyr Trp Gly Gln Gly Thr Leu Val Thr
            355                 360                 365

Val Ser Ala Ala Ser Thr Lys Gly Pro Ser Val Phe Pro Leu Ala Pro
370                 375                 380

Ser Ser Lys Ser Thr Ser Gly Gly Thr Ala Ala Leu Gly Cys Leu Val
385                 390                 395                 400

Lys Asp Tyr Phe Pro Glu Pro Val Thr Val Ser Trp Asn Ser Gly Ala
            405                 410                 415

Leu Thr Ser Gly Val His Thr Phe Pro Ala Val Leu Gln Ser Ser Gly
            420                 425                 430

Leu Tyr Ser Leu Ser Ser Val Val Glu Val Pro Ser Ser Ser Leu Gly
            435                 440                 445

Thr Gln Thr Tyr Ile Cys Asn Val Asn His Lys Pro Ser Asn Thr Lys
            450                 455                 460

Val Asp Lys Lys Val Glu Pro Lys Ser Cys Asp Lys Thr His Thr Cys
465                 470                 475                 480
```

```
Pro Pro Cys Pro Ala Pro Glu Leu Leu Gly Gly Pro Ser Val Phe Leu
            485                 490                 495

Phe Pro Pro Lys Pro Lys Asp Thr Leu Met Ile Ser Arg Thr Pro Glu
            500                 505                 510

Val Thr Cys Val Val Val Asp Val Ser His Glu Asp Pro Glu Val Lys
            515                 520                 525

Phe Asn Trp Tyr Val Asp Gly Val Glu Val His Asn Ala Lys Thr Lys
            530                 535                 540

Pro Arg Glu Glu Gln Tyr Asn Ser Thr Tyr Arg Val Val Ser Val Leu
545                 550                 555                 560

Thr Val Leu His Gln Asp Trp Leu Asn Gly Lys Glu Tyr Lys Cys Lys
            565                 570                 575

Val Ser Asn Lys Ala Leu Pro Ala Pro Ile Glu Lys Thr Ile Ser Lys
            580                 585                 590

Ala Lys Gly Gln Pro Arg Glu Pro Gln Val Tyr Thr Leu Pro Pro Ser
            595                 600                 605

Arg Glu Glu Met Thr Lys Asn Gln Val Ser Leu Thr Cys Leu Val Lys
            610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
            645                 650                 655

Ser Phe Phe Leu Tyr Ser Lys Leu Thr Val Asp Lys Ser Arg Trp Gln
            660                 665                 670

Gln Gly Asn Val Phe Ser Cys Ser Val Met His Glu Ala Leu His Asn
            675                 680                 685

His Tyr Thr Gln Lys Ser Leu Ser Leu Ser Pro Gly Lys
            690                 695                 700

<210> SEQ ID NO 15
<211> LENGTH: 214
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
```

```
            145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
        210

<210> SEQ ID NO 16
<211> LENGTH: 214
<212> TYPE: PRT
<213> ORGANISM: Homo sapiens

<400> SEQUENCE: 16

Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
                20                  25                  30
Ile His Trp Tyr Gln Gln Arg Thr Asn Gly Ser Pro Arg Leu Leu Ile
            35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
                100                 105                 110
Pro Ala Val Phe Ile Phe Pro Pro Ser Asp Glu Gln Leu Lys Ser Gly
            115                 120                 125
Thr Ala Ser Val Val Cys Leu Leu Lys Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
        210

<210> SEQ ID NO 17
<211> LENGTH: 122
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
1               5                   10                  15
Ser Leu Arg Leu Ser Cys Ala Val Ser Gly Phe Thr Phe Asn Ser Phe
                20                  25                  30
Ala Met Ser Trp Val Arg Gln Ala Pro Gly Lys Gly Leu Glu Trp Val
```

```
                35                  40                  45
Ser Ala Ile Ser Gly Ser Gly Gly Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Phe Cys
                 85                  90                  95
Ala Lys Asp Lys Ile Leu Trp Phe Gly Glu Pro Val Phe Asp Tyr Trp
             100                 105                 110
Gly Gln Gly Thr Leu Val Thr Val Ser Ser
             115                 120

<210> SEQ ID NO 18
<211> LENGTH: 702
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Phe Ser Asp Ser
             20                  25                  30
Trp Ile His Trp Val Arg Gln Ala Pro Gly Lys Gly Leu Glu Trp Val
             35                  40                  45
Ala Trp Ile Ser Pro Tyr Gly Gly Ser Thr Tyr Tyr Ala Asp Ser Val
         50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Arg His Trp Pro Gly Gly Phe Asp Tyr Trp Gly Gln Gly Thr
             100                 105                 110
Leu Val Thr Val Ser Ser Ala Ser Thr Lys Gly Pro Ser Val Phe Pro
             115                 120                 125
Leu Ala Pro Ser Ser Lys Ser Thr Ser Gly Gly Thr Ala Ala Leu Gly
         130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Glu Val Pro Ser Ser
             180                 185                 190
Ser Leu Gly Thr Gln Thr Tyr Ile Cys Asn Val Asn His Lys Pro Ser
             195                 200                 205
Asn Thr Lys Val Asp Lys Lys Val Glu Pro Lys Ser Cys Asp Lys Thr
         210                 215                 220
His Thr Ser Pro Pro Ala Pro Ala Pro Glu Leu Leu Gly Gly Pro Ala
225                 230                 235                 240
Ala Pro Pro Ala Pro Ala Pro Gly Gly Glu Val Gln Leu Leu Glu
                245                 250                 255
Ser Gly Gly Gly Leu Val Gln Pro Gly Gly Ser Leu Arg Leu Ser Cys
             260                 265                 270
Ala Val Ser Gly Phe Thr Phe Asn Ser Phe Ala Met Ser Trp Val Arg
             275                 280                 285
```

```
Gln Ala Pro Gly Lys Gly Leu Glu Trp Val Ser Ala Ile Ser Gly Ser
    290                 295                 300

Gly Gly Gly Thr Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
                325                 330                 335

Arg Ala Glu Asp Thr Ala Val Tyr Phe Cys Ala Lys Asp Lys Ile Leu
            340                 345                 350

Trp Phe Gly Glu Pro Val Phe Asp Tyr Trp Gly Gln Gly Thr Leu Val
        355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
                405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
        435                 440                 445

Gly Thr Gln Thr Tyr Ile Cys Asn Val Asn His Lys Pro Ser Asn Thr
    450                 455                 460

Lys Val Asp Lys Lys Val Glu Pro Lys Ser Cys Asp Lys Thr His Thr
465                 470                 475                 480

Cys Pro Pro Cys Pro Ala Pro Glu Leu Leu Gly Gly Pro Ser Val Phe
                485                 490                 495

Leu Phe Pro Pro Lys Pro Lys Asp Thr Leu Met Ile Ser Arg Thr Pro
            500                 505                 510

Glu Val Thr Cys Val Val Val Asp Val Ser His Glu Asp Pro Glu Val
        515                 520                 525

Lys Phe Asn Trp Tyr Val Asp Gly Val Glu Val His Asn Ala Lys Thr
    530                 535                 540

Lys Pro Arg Glu Glu Gln Tyr Asn Ser Thr Tyr Arg Val Val Ser Val
545                 550                 555                 560

Leu Thr Val Leu His Gln Asp Trp Leu Asn Gly Lys Glu Tyr Lys Cys
                565                 570                 575

Lys Val Ser Asn Lys Ala Leu Pro Ala Pro Ile Glu Lys Thr Ile Ser
            580                 585                 590

Lys Ala Lys Gly Gln Pro Arg Glu Pro Gln Val Tyr Thr Leu Pro Pro
        595                 600                 605

Ser Arg Glu Glu Met Thr Lys Asn Gln Val Ser Leu Thr Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Val Leu Asp Ser Asp
                645                 650                 655

Gly Ser Phe Phe Leu Tyr Ser Lys Leu Thr Val Asp Lys Ser Arg Trp
            660                 665                 670

Gln Gln Gly Asn Val Phe Ser Cys Ser Val Met His Glu Ala Leu His
        675                 680                 685

Asn His Tyr Thr Gln Lys Ser Leu Ser Leu Ser Pro Gly Lys
    690                 695                 700
```

```
<210> SEQ ID NO 19
<211> LENGTH: 214
<212> TYPE: PRT
<213> ORGANISM: Homo sapiens

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ala Val Phe Ile Phe Pro Pro Ser Asp Glu Gln Leu Lys Ser Gly
        115                 120                 125

Thr Ala Ser Val Val Cys Leu Leu Lys Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 214
<212> TYPE: PRT
<213> ORGANISM: Homo sapiens

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
              115                 120                 125
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 475
<212> TYPE: PRT
<213> ORGANISM: Homo sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Glu Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Ser Pro Pro Ala Pro Ala Pro Glu Leu Leu Gly Gly Pro Ala
225                 230                 235                 240

Ala Pro Pro Ala Pro Ala Pro Ala Gly Gly Glu Val Gln Leu Leu Glu
                245                 250                 255

Ser Gly Gly Gly Leu Val Gln Pro Gly Gly Ser Leu Arg Leu Ser Cys
            260                 265                 270
```

-continued

Ala Val Ser Gly Phe Thr Phe Asn Ser Phe Ala Met Ser Trp Val Arg
            275                 280                 285

Gln Ala Pro Gly Lys Gly Leu Glu Trp Val Ser Ala Ile Ser Gly Ser
    290                 295                 300

Gly Gly Gly Thr Tyr Tyr Ala Asp Ser Val Lys Gly Arg Phe Thr Ile
305                 310                 315                 320

Ser Arg Asp Asn Ser Lys Asn Thr Leu Tyr Leu Gln Met Asn Ser Leu
            325                 330                 335

Arg Ala Glu Asp Thr Ala Val Tyr Phe Cys Ala Lys Asp Lys Ile Leu
            340                 345                 350

Trp Phe Gly Glu Pro Val Phe Asp Tyr Trp Gly Gln Gly Thr Leu Val
            355                 360                 365

Thr Val Ser Ser Ala Ser Thr Lys Gly Pro Ser Val Phe Pro Leu Ala
    370                 375                 380

Pro Ser Ser Lys Ser Thr Ser Gly Gly Thr Ala Ala Leu Gly Cys Leu
385                 390                 395                 400

Val Lys Asp Tyr Phe Pro Glu Pro Val Thr Val Ser Trp Asn Ser Gly
            405                 410                 415

Ala Leu Thr Ser Gly Val His Thr Phe Pro Ala Val Leu Gln Ser Ser
            420                 425                 430

Gly Leu Tyr Ser Leu Ser Ser Val Val Thr Val Pro Ser Ser Ser Leu
            435                 440                 445

Gly Thr Gln Thr Tyr Ile Cys Asn Val Asn His Lys Pro Ser Asn Thr
    450                 455                 460

Lys Val Asp Lys Lys Val Glu Pro Lys Ser Cys
465                 470                 475

<210> SEQ ID NO 22
<211> LENGTH: 10
<212> TYPE: PRT
<213> ORGANISM: Homo sapiens

<400> SEQUENCE: 22

Pro Ser Thr Pro Pro Thr Pro Ser Pro Ser
1               5                   10

<210> SEQ ID NO 23
<211> LENGTH: 118
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

```
Ala Arg Arg His Trp Pro Gly Gly Phe Asp Tyr Trp Gly Gln Gly Thr
            100                 105                 110
Leu Val Thr Val Ser Ser
            115
```

POLYPEPTIDE LINKER FOR PREPARING MULTISPECIFIC ANTIBODIES

CROSS-REFERENCE TO RELATED APPLICATION

This application is the U.S. national stage application of International Patent Application No. PCT/EP2018/050481, filed Jan. 9, 2018.

The Sequence Listing for this application is labeled "Seq-List.txt" which was created on Jul. 5, 2019, and is 35 KB. The entire content of the sequence listing is incorporated herein by reference in its entirety.

The present invention relates to multispecific antibodies with improved properties, useful in medical field.

BACKGROUND OF THE INVENTION

Therapeutic fusion proteins have become an important modality in drug development. Frequently, peptide linkers are used to construct multi-domain proteins from different functional protein modules. The resulting multidomain proteins are designed to bind to the target cognate to the individual modules (or simultaneously exert the biological function of the individual modules) in order to either enhance the biological effects associated with the isolated single domains or to produce novel biological activities unattainable by the isolated single domains. There are numerous examples of molecules that utilize peptide linkers: single chain variable domains of antibodies (scFv), immunecytokines (cytokine-antibody fusions), bispecific antibodies (BsAb) etc. The choice of linker(s) for a specific fusion protein is dictated by considerations such as: 1) whether the linker(s) require(s) flexibility to afford folding of various domains into a particular tertiary structure (e.g. scFv-based antibodies), 2) whether the linker(s) require rigidity in order to provide a necessary separation between protein domains, or 3) whether the linker(s) must be cleavable in order to permit the separation of domains in vivo to produce the desired activity (Xiaoying Chen, et al, Adv Drug Deliv Rev. 2013. 65(10): 1357-1369). The choice of linkers can be critical since inappropriate linkers may reduce or eliminate the desired activity of the fusion protein (Yumi Maeda, et al, Anal. Biochem. 1997. 249(2): 147-152).

Various linker sequences have been identified for use in the construction of fusion proteins (Richard George and Jaap Heringa, Protein Engineering. 2003. 15(11): 871-879; Xiaoying Chen et al, Adv Drug Deliv Rev. 2013. 65(10): 1357-1369). There are also various available databases that have compiled linker sequences employed in the construction of fusion proteins: 1) SynLinker compiled by the National University of Singapore (synlinker.syncti.org), and 2) The International Genetically Engineered Machine Competition (parts.igem.org/Protein_domains/Linker); Centre for Integrative Bioinformatics at Vrije Universiteit Amsterdam (ibi.vu.nl/programs/linkerdbwww).

International patent application WO2013/005194 discloses multispecific antibodies constructed with linkers designed from the IgG1 hinge sequence, followed by the N-terminal end of the IgG1 CH2 domain sequence followed by the 8 amino acid semi-rigid linker sequence from the central part of the IgA1 hinge. This semi-rigid linker, comprising the central part of the IgA1 hinge, is important to afford for a sufficient separation of both Fab domains of the antibodies, in order to avoid steric hindrance from the C-terminal end of the exterior Fab 1 impacted on the antigen-binding paratope of the interior Fc-proximal Fab2.

However, the inventors have identified that the presence of a large number of glycoforms would not make it so easy to produce consistent preparations of such multispecific antibodies required for the development of therapeutics. Additionally, the characterization of such preparations would also be quite complex, which would make comparison of the different manufactured batches laborious.

SUMMARY OF THE INVENTION

The inventors have then realized that this could be improved, by redesigning the linker, especially by eliminating glycosylation sites from the linker.

The invention thus provides a linker polypeptide which comprises or consists of amino acid sequence EPKX$_1$CDKX$_2$HX$_3$X$_4$PPX$_5$PAPELLGGPX$_6$X$_7$PPX$_8$PX$_9$PX$_{10}$GG (SEQ ID NO: 1), wherein X$_1$, X$_2$, X$_3$, X$_4$, X$_5$, X$_6$, X$_7$, X$_8$, X$_9$, X$_{10}$, identical or different, are any amino acid as defined in herein; with the proviso that the polypeptide does not comprise nor consist of sequences EPKSCDKTHTCPPCPAPELLGGPSTPPTPSPSGG (SEQ ID NO: 5) or EPKSCDKTHTSPPSPAPELLGGPSTPPTPSPSGG (SEQ ID NO: 6).

Such polypeptide is useful as a linker in fusion proteins, more particularly multispecific, in particular bispecific, antibodies.

A subject of the invention is thus a multispecific antigen-binding fragment comprising at least two Fab fragments with different CH1 and CL domains, wherein each Fab fragment recognizes a different epitope of interest, and said Fab fragments are tandemly arranged in any order, the C-terminal end of the CH1 domain of a first Fab fragment being linked to the N-terminal end of the VH domain of the following Fab fragment through a polypeptide linker, characterized in that the polypeptide linker sequence comprises or consists of amino acid sequence EPKX1CDKX2HX3X4PPX5PAPELLGGPX6X7PP X8PX9PX10GG (SEQ ID NO: 1), wherein X1, X2, X3, X4, X5, X6, X7, X8, X9, X10, identical or different, are any amino acid; with the proviso that the linker sequence does not comprise nor consist of sequences

```
                                    (SEQ ID NO: 5)
EPKSCDKTHTCPPCPAPELLGGPSTPPTPSPSGG
or
                                    (SEQ ID NO: 6)
EPKSCDKTHTSPPSPAPELLGGPSTPPTPSPSGG.
```

It is further provided a multispecific antibody having two identical antigen-binding arms, each consisting of a multispecific antigen-binding fragment as defined herein.

In a preferred embodiment, it is provided a multispecific antibody that has an immunoglobulin-like structure, comprising:
- two identical antigen-binding arms each consisting of a multispecific antigen-binding fragment as defined herein;
- the dimerized CH2 and CH3 domains of an immunoglobulin;
- the hinge region of an IgA, IgG, or IgD, linking the C-terminal ends of CH1 domains of the antigen-binding arms to the N-terminal ends of the CH2 domains.

The invention thus more particularly provides a multi-specific, preferably a bispecific antibody, comprising two heavy chains and four light chains, wherein each heavy chain comprises a. a Fc region of an immunoglobulin comprising Hinge-CH2-CH3 domains, b. which Fc region is linked to Fab heavy chain CH1-VH of antibody 1 (Ab1) by said Hinge domain, c. which in turn is linked to Fab heavy chain CH1-VH of antibody 2 (Ab2), by a polypeptide linker sequence, wherein the polypeptide linker sequence links the N-terminus of said Fab heavy chain VH domain of Ab1 with the C-terminus of said CH1 domain of Ab2, and the four light chains comprise light chains of Ab1 and light chains of Ab2 associated with their cognate heavy chain domains;

characterized in that the polypeptide linker sequence comprises or consists of amino acid sequence EPKX$_1$CDKX$_2$HX$_3$X$_4$PPX$_5$PAPELLGGPX$_6$X$_7$PPX$_8$PX$_9$PX$_{10}$GG (SEQ ID NO: 1), wherein X$_1$, X$_2$, X$_3$, X$_4$, X$_5$, X$_6$, X$_7$, X$_8$, X$_9$, X$_{10}$, identical or different, are any amino acids; with the proviso that the linker sequence does not comprise nor consist of sequences

```
                                        (SEQ ID NO: 5)
EPKSCDKTHTCPPCPAPELLGGPSTPPTPSPSGG
or (SEQ ID NO: 6)
EPKSCDKTHTSPPSPAPELLGGPSTPPTPSPSGG.
```

In a particular embodiment, the polypeptide linker sequence comprises or consists of a sequence selected from the group consisting of

```
                                        (SEQ ID NO: 2)
EPKSCDKTHTSPPAPAPELLGGPGGPPGPGPGGG;

(SEQ ID NO: 3)
EPKSCDKTHTSPPAPAPELLGGPAAPPAPAPAGG;
and (SEQ ID NO: 4)
EPKSCDKTHTSPPAPAPELLGGPAAPPGPAPGGG.
```

A further subject of the invention is a polypeptide which comprises, preferably consists of, a heavy chain of the multispecific antigen-binding fragment, or multispecific, preferably bispecific antibody, as defined herein.

The invention further provides a polynucleotide comprising a sequence encoding such polypeptide.

A host cell transfected with an expression vector comprising said polynucleotide is also part of the invention.

A further subject of the invention is a method for producing a multispecific antibody, preferably a bispecific antibody, as described herein, said method comprising the following steps: a) culturing in suitable medium and culture conditions a host cell expressing an antibody heavy chain as defined herein, and an antibody light chain as defined herein; and b) recovering said produced antibodies from the culture medium or from said cultured cells.

LEGENDS TO THE FIGURES

FIG. 4A shows the MS spectrum of the LC-MS analysis of Fab-Fab3a.

FIG. 5A shows the MS spectrum of the LC-MS analysis of BiXAb3a.

DETAILED DESCRIPTION OF THE INVENTION

Definitions

Figure 1:
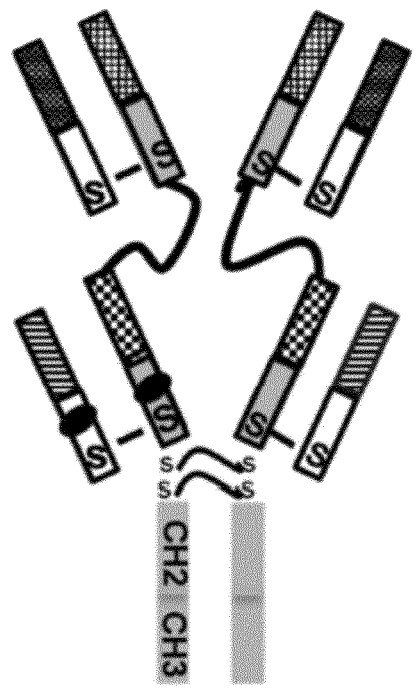
FIG. 1 is a schematic drawing of a full-length BiXAb bispecific antibody of the invention.

The basic structure of a naturally occurring antibody molecule is a Y-shaped tetrameric quaternary structure consisting of two identical heavy chains and two identical light chains, held together by non-covalent interactions and by inter-chain disulfide bonds.

In mammalian species, there are five types of heavy chains: α, δ, ε, γ, and μ, which determine the class (isotype) of immunoglobulin: IgA, IgD, IgE, IgG, and IgM, respectively. The heavy chain N-terminal variable domain (VH) is followed by a constant region, containing three domains (numbered CH1, CH2, and CH3 from the N-terminus to the C-terminus) in γ, α, and δ heavy chains, while the constant regions of μ and ε heavy chains are composed of four domains (numbered CH1, CH2, CH3 and CH4 from the N-terminus to the C-terminus). The CH1 and CH2 domains of IgA, IgG, and IgD are separated by a flexible hinge, which varies in length between the different classes and in the case of IgA and IgG, between the different subtypes: IgG1, IgG2, IgG3, and IgG4 have respectively hinges of 15, 12, 62 (or 77), and 12 amino acids, and IgA1 and IgA2 have respectively hinges of 20 and 7 amino acids.

There are two types of light chains: λ and κ, which can associate with any of the heavy chain isotypes, but are both of the same type in a given antibody molecule. Both light chains appear to be functionally identical. Their N-terminal variable domain (VL) is followed by a constant region consisting of a single domain termed CL.

The heavy and light chains pair by protein/protein interactions between the CH1 and CL domains, and between the VH and VL domains, and the two heavy chains associate by protein/protein interactions between their CH3 domains.

The antigen-binding regions correspond to the arms of the Y-shaped structure, which consist each of the complete light chain paired with the VH and CH1 domains of the heavy chain, and are called the Fab fragments (for Fragment antigen binding). Fab fragments were first generated from native immunoglobulin molecules by papain digestion which cleaves the antibody molecule in the hinge region, on the amino-terminal side of the interchain disulfide bonds, thus releasing two identical antigen-binding arms. Other proteases such as pepsin, also cleave the antibody molecule in the hinge region, but on the carboxy-terminal side of the interchain disulfide bonds, releasing fragments consisting of two identical Fab fragments and remaining linked through disulfide bonds; reduction of disulfide bonds in the F(ab')2 fragments generate Fab' fragments.

The part of the antigen-binding region corresponding to the VH and VL domains is called the Fv fragment (for Fragment variable); it contains the CDRs (complementarity determining regions), which form the antigen-binding site (also termed paratope).

The effector region of the antibody which is responsible for its binding to effector molecules on immune cells, corresponds to the stem of the Y-shaped structure, and contains the paired CH2 and CH3 domains of the heavy chain (or the CH2, CH3 and CH4 domains, depending on the class of antibody), and is called the Fc (for Fragment crystallisable) region.

Due to the identity of the two heavy chains and the two light chains, naturally occurring antibody molecules have two identical antigen-binding sites and thus bind simultaneously to two identical epitopes.

In the context of the invention, the "multispecific antigen-binding fragment" is defined herein as a molecule having two or more antigen-binding regions, each recognizing a different epitope. The different epitopes can be borne by a same antigenic molecule or by different antigenic molecules. The term "recognizing" or "recognizes" means that the fragment specifically binds a target antigen.

An antibody "specifically binds" to a target antigen if it binds with greater affinity, avidity, more readily, and/or with greater duration than it binds to other substances. "Specific binding" or "preferential binding" does not necessarily require (although it can include) exclusive binding. Generally, but not necessarily, reference to binding means preferential binding.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

The term "treatment" or "treating" refers to an action, application or therapy, wherein a subject, including a human being, is subjected to medical aid with the purpose of improving the subject's condition, directly or indirectly. Particularly, the term refers to reducing incidence, or alleviating symptoms, eliminating recurrence, preventing recurrence, preventing incidence, improving symptoms, improving prognosis or combination thereof in some embodiments. The skilled artisan would understand that treatment does not necessarily result in the complete absence or removal of symptoms. For example, with respect to cancer, "treatment" or "treating" may refer to slowing neoplastic or malignant cell growth, proliferation, or metastasis, preventing or delaying the development of neoplastic or malignant cell growth, proliferation, or metastasis, or some combination thereof.

Design of the Multispecific Antibodies

It is herein provided multispecific antigen-binding fragment(s) and multispecific antibody constructs, comprising said fragments, wherein each multispecific antigen-binding fragment consists essentially of tandemly arranged Fab fragments, separated by the linker of the invention.

Such fragments and constructs preferably comprise chains from human immunoglobulins, preferably IgG, still preferably IgG1.

In case of a multispecific antigen-binding fragment comprising more than two different Fab fragments, the polypeptide linkers separating the Fab fragments can be identical or different.

According to a preferred embodiment of a multispecific antibody of the invention, it has two identical antigen-binding arms, each consisting of a multispecific antigen-binding fragment as defined above. The antigen-binding arms can be linked together in diverse ways, depending on the intended use for the antibody.

If one wishes to obtain an antibody without Fc-mediated effects, the antibody will comprise no Fc region. In this case, the two antigen-binding arms can be linked together for instance:

by homodimerization of the antigen-binding arms through the inter-chain disulfide bonds provided by the polypeptide linker(s) separating the Fab fragments; and/or through the addition at the C-terminal end of each antigen-binding arm, of a polypeptide extension containing cysteine residues allowing the formation of inter-chain disulfide bonds, and homodimerization of said polypeptide extension resulting in a hinge-like structure; by way of non-limiting examples, said polypeptide extension may be for instance a hinge sequence of an IgG1, IgG2 or IgG3;

through a semi-rigid linker joining the C-terminal ends of the heavy chains of the two antigen-binding arms to form a single polypeptide chain and maintaining said antigen-binding arms at a sufficient distance between each other.

Alternatively, if effector functions such as CDC, ADCC or ADP are desired, a multispecific antibody of the invention can further comprise a Fc domain providing these effector functions. The choice of the Fc domain will depend on the type of desired effector functions.

In this case, a multispecific antibody of the invention has an immunoglobulin-like structure, comprising:

two identical multispecific antigen-binding arms as defined above;

the dimerized CH2 and CH3 domains of an immunoglobulin;

either the hinge region of an IgA, IgG, or IgD, linking the C-terminal ends of the CH1 domains of the antigen-binding arms to the N-terminal ends of the CH2 domains, or alternatively, when the CH4 domains that follow the CH3 domains come from an IgM or IgE, the C-terminal ends of the CH1 domains of the antigen-binding arms being in this case can be linked directly to the N-terminal ends of the CH2 domains.

Preferably, the CH2 and CH3 domains, the hinge region and/or the CH4 domains are derived from a same immunoglobulin or from immunoglobulins of the same isotype and subclass as the CH1 domains of the antigen-binding arm.

The CH2, CH3, and optionally CH4 domains, as well as the hinge regions from native immunoglobulins can be used. It is also possible to mutate them, if desired, for instance in order to modulate the effector function of the antibody. In some instances, whole or part of the CH2 or the CH3 domain can be omitted.

The invention more particularly provides bispecific tetravalent antibodies, comprising two binding sites to each of their targets, and a functional Fc domain allowing the activation of effector functions such as antibody-dependent cell-mediated cytotoxicity (ADCC) and phagocytosis.

Such preferred antibodies of the invention are full length antibodies. They preferably comprise heavy chains and light chains from human immunoglobulins, preferably IgG, still preferably IgG1.

The light chains may be lambda or kappa light chains; they preferably are Kappa light chains.

In a preferred embodiment, the linker of the invention links IgG Fab domains in a tetra-Fab bispecific antibody format, the amino acid sequence of which comprises the heavy chain sequences of at least two Fab joined by said polypeptide linker, followed by the native hinge sequence, followed by the IgG Fc sequence, co-expressed with the appropriate IgG light chain sequences.

An example of the antibodies of the invention, named BiXAb antibodies, which have an IgG-like structure, is illustrated in FIG. 1. Antibodies designated BiXAb2a, BiXAb2b, BiXAb2c, and BiXAb3b, described below, are particular examples.

The bispecific antibodies of the invention typically comprise
- a continuous heavy chain constructed of an Fc (Hinge-CH2-CH3),
- followed by antibody 1 Fab heavy chain (CH1-VH) and the successive Fab heavy chain (CH1-VH) of antibody 2, the latter joined by a polypeptide linker sequence of the invention,
- and during protein expression the resulting heavy chain assembles into dimers while the co-expressed antibody 1 and antibody 2 light chains (VL-CL) associate with their cognate heavy chains to form the final tandem Fab-Fab-Fc molecule, the antibody 1 (Ab1) and the antibody 2 (Ab2) being different.

In a preferred embodiment, described are bispecific antibodies, which comprise
- two Fab fragments with different CH1 and CL domains consisting of
  - a) Fab fragment having CH1 and C-Kappa domains derived from a human IgG1/Kappa, and the VH and VL domains of Ab1,
  - b) Fab fragment having CH1 and C-Kappa domains derived from a human IgG1/Kappa and the VH and VL domains of Ab2,
  - c) a mutated light chain CL constant domain which is derived from human Kappa constant domain,
  - d) a mutated heavy chain CH1 constant domain the Fab fragments being tandemly arranged in the following order
    - the C-terminal end of the CH1 domain of Ab1 Fab fragment being linked to the N-terminal end of the VH domain of Ab2 Fab fragment through a polypeptide linker,
    - the hinge region of a human IgG1 linking the C-terminal ends of CH1 domain of Ab2 fragment to the N-terminal of the CH2 domain,
    - the dimerized CH2 and CH3 domains of a human IgG1.

Ab1 and Ab2 may be any antibody of interest, especially any antibody of therapeutic interest.

In a particular embodiment, Ab1 and Ab2, being different, independently are selected from the group consisting of an anti-EGFR antibody and an anti-HER2/neu antibody. In a preferred embodiment, Ab1 and Ab2, being different, independently are selected from the group consisting of cetuximab or a mutated derivative thereof, on the one hand, and trastuzumab, or a mutated derivative thereof, on the other hand.

In another particular embodiment, Ab1 and Ab2, being different, independently are selected from the group consisting of an anti-CD38 antibody and an anti-PD-L1 antibody.

Such antibodies are useful as a medicament, more particularly in treating a cancer.

Throughout the present description, amino acid sequences are defined according to Kabat et al, Sequences of Proteins of Immunological Interest, 5th Ed. Public Health Service, National Institutes of Health, Bethesda, Md. (1991).

Figure 2:
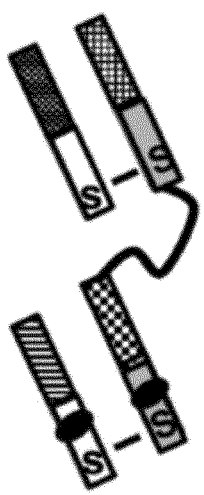
FIG. 2 is a schematic drawing of a bispecific construct that contains only two Fab domains connected by a linker without a Fc-domain (Fab-Fab).

Another example of the constructs of the invention, which is a multispecific antigen-binding fragment Fab-Fab, which does not contain the Fc domain, is illustrated in FIG. 2. A particular example, designated Fab-Fab3a, is described below.

Such Fab-Fab constructs typically comprise two different Fab domains. Such antibodies possess only one Fab domain each that binds to antigen 1 and to antigen 2. They possess the same Light Chains as in the corresponding BiXAb antibodies; however, the Heavy Chain of Fab-Fabs is shortened in such a fashion so that their most C-terminal residue is Cysteine-220 (in EU numbering).

Design of the Linkers

The polypeptide linker sequence according to the invention comprises or consists of amino acid sequence EPKX$_1$CDKX$_2$HX$_3$X$_4$PPX$_5$PAPELLGGPX$_6$X$_7$PPX$_8$PX$_9$PX$_{10}$GG (SEQ ID NO: 1), wherein X$_1$, X$_2$, X$_3$, X$_4$, X$_5$, X$_6$, X$_7$, X$_8$, X$_9$, X$_{10}$, identical or different, are any amino acid; with the proviso that the linker sequence does not comprise nor consist of sequences

```
                                            (SEQ ID NO: 5)
EPKSCDKTHTCPPCPAPELLGGPSTPPTPSPSGG
or
                                            (SEQ ID NO: 6)
EPKSCDKTHTSPPSPAPELLGGPSTPPTPSPSGG.
```

The polypeptide linker sequence consists of less than 80 amino acids, preferably less than 60 amino acids, still preferably less than 40 amino acids.

In a particular embodiment, X$_1$, X$_2$ and X$_3$, identical or different, are Threonine (T) or Serine (S).

In another particular embodiment, X$_1$, X$_2$ and X$_3$, identical or different, are any amino acids other than Threonine (T) or Serine (S), preferably wherein X$_1$, X$_2$ and X$_3$, identical or different, are selected from the group consisting of Ala (A), Gly (G), Val (V), Asn (N), Asp (D) and Ile (I), still preferably X$_1$, X$_2$ and X$_3$, identical or different, may be Ala (A) or Gly (G).

Alternatively, X$_1$, X$_2$ and X$_3$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a particular embodiment, X$_4$ and X$_5$, identical or different, are any amino acid selected from the group consisting of Serine (S), Cysteine (C), Alanine (A), and Glycine (G).

In a preferred embodiment, X$_4$ is Serine (S) or Cysteine (C).

In a preferred aspect, X$_5$ is Alanine (A) or Cysteine (C).

In a particular embodiment, X$_6$, X$_7$, X$_8$, X$_9$, X$_{10}$, identical or different, are any amino acid other than Threonine (T) or Serine (S). Preferably X$_6$, X$_7$, X$_8$, X$_9$, X$_{10}$, identical or different, are selected from the group consisting of Ala (A), Gly (G), Val (V), Asn (N), Asp (D) and Ile (I).

Alternatively, X$_6$, X$_7$, X$_8$, X$_9$, X$_{10}$, identical or different, may be Leu (L), Glu (E), Gln (Q), Met (M), Lys (K), Arg (R), Phe (F), Tyr (T), His (H), Trp (W), preferably Leu (L), Glu (E), or Gln (Q).

In a preferred embodiment, X$_6$, X$_7$, X$_8$, X$_9$, X$_{10}$, identical or different, are selected from the group consisting of Ala (A) and Gly (G).

In still a preferred embodiment, X$_6$ and X$_7$ are identical and are preferably selected from the group consisting of Ala (A) and Gly (G).

In a preferred embodiment, the polypeptide linker sequence comprises or consists of sequence SEQ ID NO: 1, wherein $X_1$, $X_2$ and $X_3$, identical or different, are Threonine (T), Serine (S);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

In a particular embodiment, the polypeptide linker sequence comprises or consists of a sequence selected from the group consisting of

EPKSCDKTHTSPPAPAPELLGGPGGPPGPGPGGG; (SEQ ID NO: 2)

EPKSCDKTHTSPPAPAPELLGGPAAPPAPAPAGG; (SEQ ID NO: 3)
and

EPKSCDKTHTSPPAPAPELLGGPAAPPGPAPGGG. (SEQ ID NO: 4)

In another preferred embodiment, the polypeptide linker sequence comprises or consists of sequence SEQ ID NO: 1, wherein $X_1$, $X_2$ and $X_3$, identical or different, are Ala (A) or Gly (G);

$X_4$ is Serine (S) or Cysteine (C);

$X_5$ is Alanine (A) or Cysteine (C);

$X_6$, $X_7$, $X_8$, $X_9$, $X_{10}$, identical or different, are selected from the group consisting of Ala (A) and Gly (G).

Production of the Antibodies

Nucleic acids encoding heavy and light chains of the antibodies of the invention are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

In one example, both the heavy and light chain coding sequences (e.g., sequences encoding a VH and a VL, a VH-CH1 or a VL-CL, are included in one expression vector. In another example, each of the heavy and light chains of the antibody is cloned into an individual vector. In the latter case, the expression vectors encoding the heavy and light chains can be co-transfected into one host cell for expression of both chains, which can be assembled to form intact antibodies either in vivo or in vitro.

In a particular embodiment, a host cell is co-transfected with three independent expression vectors, such as plasmids, leading to the coproduction of all three chains (namely the heavy chain HC, and two light chains LC1 and LC2, respectively) and to the secretion of the multispecific antibody.

More especially the three vectors may be advantageously used in a following molecular ratio of 3:2:2 (HC:LC1:LC2).

The recombinant vectors for expression of the antibodies described herein typically contain a nucleic acid encoding the antibody amino acid sequences operably linked to a promoter, either constitutive or inducible. The vectors can be suitable for replication and integration in prokaryotes, eukaryotes, or both. Typical vectors contain transcription and translation terminators, initiation sequences, and promoters useful for regulation of the expression of the nucleic acid encoding the antibody. The vectors optionally contain generic expression cassettes containing at least one independent terminator sequence, sequences permitting replication of the cassette in both eukaryotes and prokaryotes, i.e., shuttle vectors, and selection markers for both prokaryotic and eukaryotic systems.

Multispecific antibodies as described herein may be produced in prokaryotic or eukaryotic expression systems, such as bacteria, yeast, filamentous fungi, insect, and mammalian cells.

It is not necessary that the recombinant antibodies of the invention be glycosylated or expressed in eukaryotic cells; however, expression in mammalian cells is generally preferred. Examples of useful mammalian host cell lines are human embryonic kidney line (293 cells), baby hamster kidney cells (BHK cells), Chinese hamster ovary cells/− or +DHFR (CHO, CHO-S, CHO-DG44, Flp-in CHO cells), African green monkey kidney cells (VERO cells), and human liver cells (Hep G2 cells).

Mammalian tissue cell culture is preferred to express and produce the polypeptides because a number of suitable host cell lines capable of secreting intact immunoglobulins have been developed in the art, and include the CHO cell lines, various Cos cell lines, HeLa cells, preferably myeloma cell lines, or transformed B-cells or hybridomas.

In a most preferred embodiment, the multispecific, preferably bispecific, antibodies of the invention are produced by using a CHO cell line, most advantageously a CHO-S cell line.

Expression vectors for these cells can include expression control sequences, such as an origin of replication, a promoter, and an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example calcium phosphate treatment or electroporation may be used for other cellular hosts. (See generally Sambrook et al., Molecular Cloning: A Laboratory Manual (Cold Spring Harbor Press, 2nd ed., 1989). When heavy and light chains are cloned on separate expression vectors, the vectors are co-transfected to obtain expression and assembly of intact immunoglobulins.

Host cells are transformed or transfected with the vectors (for example, by chemical transfection or electroporation methods) and cultured in conventional nutrient media (or modified as appropriate) for inducing promoters, selecting transformants, or amplifying the genes encoding the desired sequences.

Once expressed, the whole antibodies, their dimers, individual light and heavy chains, or other immunoglobulin forms of the present invention can be further isolated or purified to obtain preparations that are substantially homogeneous for further assays and applications.

Standard protein purification methods known in the art can be used. For example, suitable purification procedures may include fractionation on immunoaffinity or ion-exchange columns, ethanol precipitation, high-performance liquid chromatography (HPLC), sodium dodecyl sulfate polyacrylamide gel electrophoresis (SDS-PAGE), ammonium sulfate precipitation, and gel filtration (see generally Scopes, Protein Purification (Springer-Verlag, N.Y., 1982). Substantially pure immunoglobulins of at least about 90 to 95% homogeneity are preferred, and 98 to 99% or more homogeneity most preferred, for pharmaceutical uses.

In vitro production allows scale-up to give large amounts of the desired multispecific, preferably bispecific, antibodies of the invention. Such methods may employ homogeneous suspension culture, e.g. in an airlift reactor or in a continuous stirrer reactor, or immobilized or entrapped cell culture, e.g. in hollow fibers, microcapsules, on agarose microbeads or ceramic cartridges.

Therapeutic Applications

A further aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention.

In another aspect, the present invention provides a composition, e.g. a pharmaceutical composition, containing an antibody as defined herein, formulated together with a pharmaceutical carrier.

A composition of the present invention can be administered by a variety of methods known in the art.

The present invention, thus generally described above, will be understood more readily by reference to the following examples, which are provided by way of illustration and are not intended to be limiting of the instant invention.

Examples

Design

A first bispecific antibody of the invention is the antibody designated BiXAb2a having the following structure:
i) a continuous heavy chain which comprises
Trastuzumab heavy chain variable region (VH) corresponding to SEQ ID NO: 7
Wild-type CH1 constant domain (the residue at Kabat position 192 is threonine) from human IgG1 corresponding to SEQ ID NO: 8
Polypeptide linker joining the 2 Fab heavy chains consisting of (SEQ ID NO: 2)
EPKSCDKTHTSPPAPAPELLGGPGGPPGPGPGGG;

Cetuximab heavy chain variable region (VH) corresponding to SEQ ID NO: 9
Mutated CH1 constant domain (the residue at Kabat position 192 has been mutated from threonine to glutamic acid) from human IgG1 corresponding to SEQ ID NO: 10
Wild-type Hinge region from human IgG1 corresponding to SEQ ID NO: 11
Wild-type CH2 domain of human IgG1 corresponding to SEQ ID NO: 12
Wild-type CH3 domain of human IgG1 corresponding to SEQ ID NO:13

So, the bispecific antibody of the invention has a continuous heavy chain (701 residues) of SEQ ID NO: 14
ii) a wild-type trastuzumab light chain which consists of SEQ ID NO: 15
iii) a cetuximab light chain with a mutated constant domain (the residues at Kabat positions Ser 114 and Asn 137 have been mutated to Ala and Lys, respectively) from human Kappa corresponding to SEQ ID NO: 16.

A second bispecific antibody of the invention is the antibody designated BiXAb2b which is comprised of the same sequences, except for the linker, which is (SEQ ID NO: 3)
EPKSCDKTHTSPPAPAPELLGGPAAPPAPAPAGG.

A third bispecific antibody of the invention is the antibody designated BiXAb2c which is comprised of the same sequences, except for the linker, which is (SEQ ID NO: 4)
EPKSCDKTHTSPPAPAPELLGGPAAPPGPAPGGG.

A fourth bispecific antibody of the invention is the antibody designated BiXAb3b having the following structure:
i) a continuous heavy chain which comprises
Atezolizumab heavy chain variable region (VH) corresponding to SEQ ID NO: 23

(EVQLVESGGGLVQPGGSLRLSCAASGFTFSDSWIHWVRQAPGKGLEWVA
WISPYGGSTYYADSVKGRFTISADTSKNTAYLQMNSLRAEDTAVYYCARR
HWPGGFDYWGQGTLVTVSS)

Mutated CH1 constant domain (the residue at Kabat position 192 has been mutated from threonine to glutamic acid) from human IgG1 corresponding to SEQ ID NO: 10
Polypeptide linker joining the 2 Fab heavy chains consisting of SEQ ID NO: 3; Daratumumab heavy chain variable region (VH) corresponding to SEQ ID NO: 17

(EVQLLESGGGLVQPGGSLRLSCAVSGFTFNSFAMSWVRQAPGKGLEWVS
AISGSGGGTYYADSVKGRFTISRDNSKNTLYLQMNSLRAEDTAVYFCAKD
KILWFGEPVFDYWGQGTLVTVSS)

Wild-type CH1 constant domain (the residue at Kabat position 192 is threonine) from human IgG1 corresponding to SEQ ID NO: 8
Wild-type Hinge region from human IgG1 corresponding to SEQ ID NO: 11
Wild-type CH2 domain of human IgG1 corresponding to SEQ ID NO: 12
Wild-type CH3 domain of human IgG1 corresponding to SEQ ID NO:13 [So the heavy chain of the invention has a continuous heavy chain of SEQ ID NO: 18

EVQLVESGGGLVQPGGSLRLSCAASGFTFSDSWIHwVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVEVPSSSLGTQTYI

CNVNHKPSNTKVDKKVEPKSCDKTHTSPPAPAPELLGGPAAPPAPAPAGG

EVQLLESGGGLVQPGGSLRLSCAVSGFTFNSFAMSWVRQAPGKGLEWVSA

-continued

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK]

ii) an atezolizumab light chain with a mutated constant domain (the residues at Kabat positions Ser 114 and Asn 137 have been mutated to Ala and Lys, respectively) from human Kappa corresponding to SEQ ID NO: 19

DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPAVFIFPPSDEQLKSGTASVVCLLKNFYPREAKVQWKV

DNALQSGNSQESVTEQDSKDSTYSLSSTLTLSKADYEKHKVYACEVTHQG

LSSPVTKSFNRGEC iii) a wild-type daratumumab light chain which consists of SEQ ID NO: 20

EIVLTQSPATLSLSPGERATLSCRASQSVSSYLAVVYQQKPGQAPRLLIY

DASNRATGIPARFSGSGSGTDFTLTISSLEPEDFAVYYCQQRSNWPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC.

For comparison purposes, an antibody designated BiXAb3a was also produced which differs from the BiXAb3b antibody by the linker which consists of (SEQ ID NO: 6)
EPKSCDKTHTSPPSPAPELLGGPSTPPTPSPSGG.

Another construct of the invention is designated Fab-Fab3b; it is comprised of the same sequence as BiXAb3b, except that the hinge, CH2 and CH3 domains are missing in the heavy chain. So, Fab-Fab3b has a continuous heavy chain of SEQ ID NO: 21

EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVEVPSSSLGTQTYI

CNVNHKPSNTKVDKKVEPKSCDKTHTSPPAPAPELLGGPAAPPAPAPAGG

EVQLLESGGGLVQPGGSLRLSCAVSGFTFNSFAMSWVRQAPGKGLEWSA

-continued

ISGSGGGTYYADSVKGRFTISRDNSKNTLYLQMNSLRAEDTAVYFCAKDK

ILWFGEPVFDYWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSC.

For comparison purposes, the construct designated Fab-Fab3a was also produced, that is comprised of the same sequence as BiXAb3a, except that the hinge, CH2 and CH3 domains are missing in the heavy chain.

SEQ ID NO: 7 to 16 are shown below.

SEQ ID NO: 7
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

SEQ ID NO: 8
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKV

SEQ ID NO: 9
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSA

SEQ ID NO: 10
ASTKGPSVFPLAPSSKSTSGGTAALGCLVKDYFPEPVTVSWNSGALTSGV

HTFPAVLQSSGLYSLSSVVEVPSSSLGTQTYICNVNHKPSNTKVDKKV

SEQ ID NO: 11
EPKSCDKTHTCPPCP

SEQ ID NO: 12
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK

SEQ ID NO: 13
GQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKS

LSLSPGK

SEQ ID NO: 14
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTSPPAPAPELLGGPGGPPGPGPG

GGQVQLKQSGPGLVQPSQSLSITCTVSGFSLTNYGVHWVRQSPGKGLEWL

GVIWSGGNTDYNTPFTSRLSINKDNSKSQVFFKMNSLQSNDTAIYYCARA

LTYYDYEFAYWGQGTLVTVSAASTKGPSVFPLAPSSKSTSGGTAALGCLV

KDYFPEPVTVSWNSGALTSGVHTFPAVLQSSGLYSLSSVVEVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

-continued
NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 15
DIQMTQSPSSLSASVGDRVTITCRASQDVNTAVAWYQQKPGKAPKWYSAS

FLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLS

SPVTKSFNRGEC

SEQ ID NO: 16
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPAVFIFPPSDEQLKSGTASVVCLLKNFYPREAKVQWKV

DNALQSGNSQESVTEQDSKDSTYSLSSTLTLSKADYEKHKVYACEVTHQG

LSSPVTKSFNRGEC

Gene Synthesis

The amino acid sequences of anti-HER2 (trastuzumab, clone humAb4D5-8) and anti-EGFR (cetuximab) were used to design the DNA sequences after codon optimization for mammalian expression using GeneScript program. For the heavy chain, the DNAs encoding signal peptides, variable region and constant CH1 domain of Fab1 followed the pseudo hinge linker and variable region and constant CH1 domain of Fab2 with flanking sequences for restriction enzyme digestion were synthesized by GeneScript. For the light chain, the DNAs encoding signal peptides and variable and constant Kappa regions were synthesized by GeneScript.

PCR reactions using PfuTurbo Hot Start were carried out to amplify the inserts which were then digested by NotI+ApaI and NotI+HindIII for heavy and light chains, respectively. The double digested heavy chain fragments were ligated with NotI+ApaI treated pcDNA3.1 expression vector (Invitrogen) in which the human IgG1 CH1+hinge+CH2+CH3 domains were already inserted. The double digested light chain fragments were ligated with NotI+HindIII treated pcDNA3.1 expression vector (Invitrogen). Plasmid DNAs were verified by double strand DNA sequencing.

Expression and Purification

The bispecific antibodies of the invention were produced by means of transient gene expression by co-transfection of 3 genes coded on separate vectors in a 2:3:3=HC:LC1:LC2 molar ratio (1 continuous heavy chain (HC) and 2 light chains (LC)) in CHO-S cells adapted to serum-free medium in suspension (CHO SFM-II medium from Life Technologies™). Typically, for 50 mL medium scale expression testing, a total of 50 μg of plasmid DNAs (25 μg heavy chain1, 12.5 μg of tratuzumab light chain and 12.5 μg of cetuximab light chain) were mixed in 1.5 mL Eppendorf tube, 1 mL of CHO SFM medium containing 25 μL of 3 mg/mL PEI transfection reagent (POLYPLUS) pH7.0 was added, incubated at RT for 20 min. The mixture of DNA-PEI was loaded into 49 mL of Life Technologies' Invitrogen FreeStyle™ CHO-S cells at 1-2×10$^6$/mL in 125 mL shaking flask. Cells were shaken for 6 more days. The supernatant was harvested by centrifuging cells at 3,000 rpm for 15 min. The expression titer of the BiXAbs in the supernatant was determined using ForteBio's protein A biosensors (Octet® Systems). The bispecific monoclonal antibody (BiXAb) was then purified on protein A affinity medium using Mab Select SuRe (GE Healthcare Life Sciences). The antibody was eluted from protein A using 0.1 M glycine pH 3.5 with neutralization in 1 M TRIS. The purified antibody in Dulbecco's PBS (Lonza BE17-512Q) was sterile-filtered (0.2 μM sterile filters from Techno Plastic Products AG) and the final concentration determined by OD reading at 280 nm using Eppendorf BioSpectrometer®.

SDS-PAGE Analysis

Electrophoresis was performed under reducing conditions and non-reducing conditions employing Gel Biorad Stain-Free 4-15% gels and the corresponding running buffer. Samples were prepared by combining the purified BiXAb or Fab-Fab antibodies with 2×SDS sample buffer and heating for 5 min at 95° C. Preparation of reduced samples included the addition of NuPAGE reducing agent prior to heating. The apparent MW was determined using Ladder Precision Plus Protein Unstained Standards (Biorad).

Size Exclusion Chromatography Analysis

Protein aggregation is frequently observed in engineered protein molecules. We performed analytical size exclusion chromatography (SEC) to assay the high molecular weight species content of our antibodies. We employed an SEC-s3000 (300×7.8 mm) column (BioSep) and an Aktapurifier 10 system (GE Healthcare); the assay was conducted at a flow rate of 1 mL/min using PBS buffer pH 7.4.

Figure 3A:
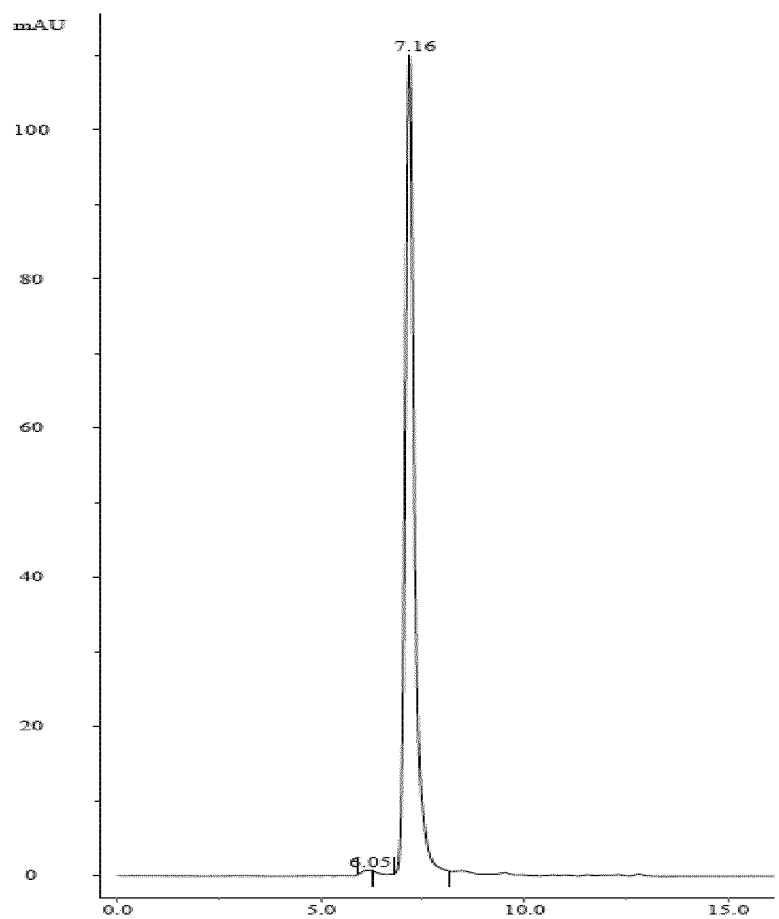
FIG. 3A shows the Size Exclusion chromatography analysis of BiXAb2b.
Figure 3B:
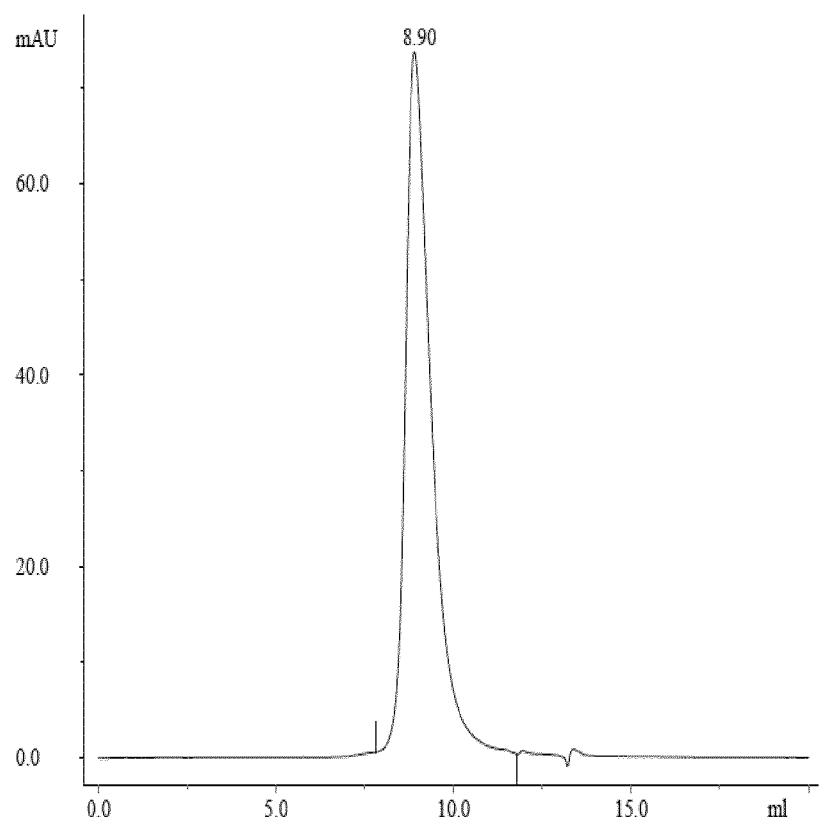
FIG. 3B shows the Size Exclusion chromatography analysis of BiXAb3b.
Figure 3C:
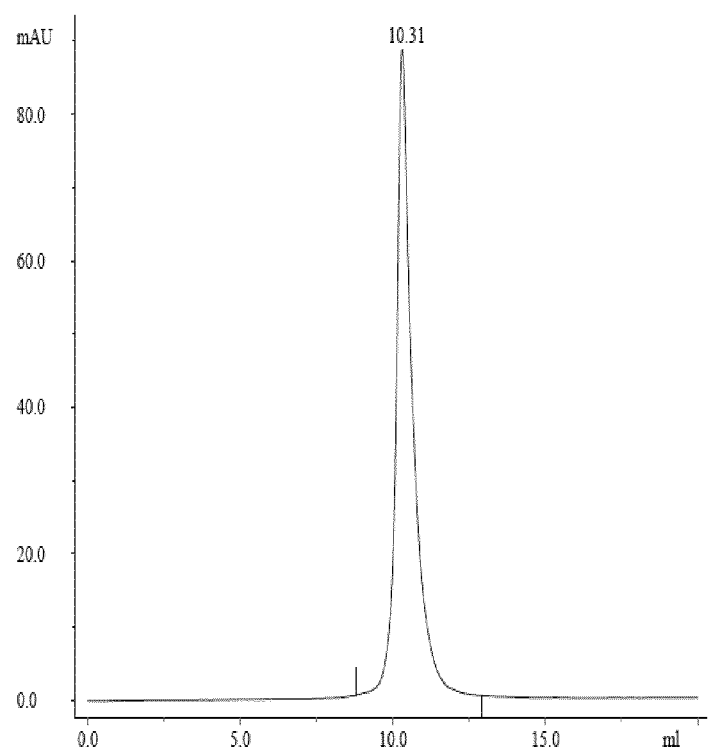
FIG. 3C shows the Size Exclusion chromatography analysis of Fab-Fab3b.

The SEC chromatograms of BiXAb2b (FIG. 3A), BiXAb3a, BiXAb3b (FIG. 3B), Fab-Fab3a, and Fab-Fab3b (FIG. 3C) demonstrated that the main peak corresponded to the expected sizes of the monomeric BiXAb and Fab-Fab antibodies; these peaks represented 99.9-100.0% of the total sample. Thus, we concluded that the antibodies containing the new linker possess no high molecular weight species. The narrow and symmetric shape of the monomeric peaks suggested that all BiXAbs and Fab-Fabs were correctly assembled and represented by a single species.

Characterization of BiXAbs by Differential Scanning Calorimetry

Differential Scanning calorimetry (DSC) was used to test the thermal stability of BiXAb2b. A Microcal™ VP-Capillary DSC system (Malvern Instruments) was used to perform differential scanning calorimetry experiments.

Samples were centrifuged (20,000× g, 5 min, 4° C.), and their protein content was quantitated prior to the DSC analysis using a NANODROP ND-1000 spectrophotometer (THERMO SCIENTIFIC) employing the IgG analysis program. For assay, samples were diluted in PBS to a final concentration of 1 mg/mL.

The pre-equilibration time was 3 min, and the resulting thermograms were acquired between 20 and 110° C. at a scan rate of 60° C./h, a filtering period of 25 sec, and medium feedback. Prior to sample analysis, 5 buffer/buffer scans were measured to stabilize the instrument, and a buffer/buffer scan was performed between each protein/buffer scan. The data were fit to a non-2-state unfolding model, with the pre- and post-transition adjusted by subtraction of the baseline.

The DSC results demonstrated that the DSC profile of BiXAb2b exhibited two transitions.

The smaller peak had a Cp max of 96 Kcal/mole/° C. and a Tm1 of 71.5° C., corresponding to the unfolding of both CH2 and Fab domains, and the larger peak had a Cp max of 190 Kcal/mole/° C. and a Tm2 of 80.5° C., corresponding to the unfolding of the CH3 domain.

Liquid Chromatography/Mass Spectroscopy (LC-MS) Analysis

LC-MS/MS data were acquired using a Dionex Ultimate 3000 system coupled to a Q-EXACTIVE mass spectrometer (Thermo Fisher Scientific, Bremen, Germany) and a PROSWIFT RP-4H reverse phase column (250 mm×1 mm; Thermo Fisher). The column oven temperature was set to 65° C. Ten microliters were injected for LC separation. A gradient of mobile phases consisting of LC-MS-grade water with 0.1% formic acid (phase A) and acetonitrile with 0.1% formic acid (phase B) was delivered at a flow rate of 0.2 mL/min (total run time of 20 minutes). Eluted antibody species were introduced into the Q-EXACTIVE instrument by electrospray ionization (ESI), which operated in positive ion mode using full-scan 15,000 resolution. Xcalibur 2.2 software (Thermo Fisher Scientific, Bremen, Germany) was used for instrument control and processing of the data files.

Figure 4A:
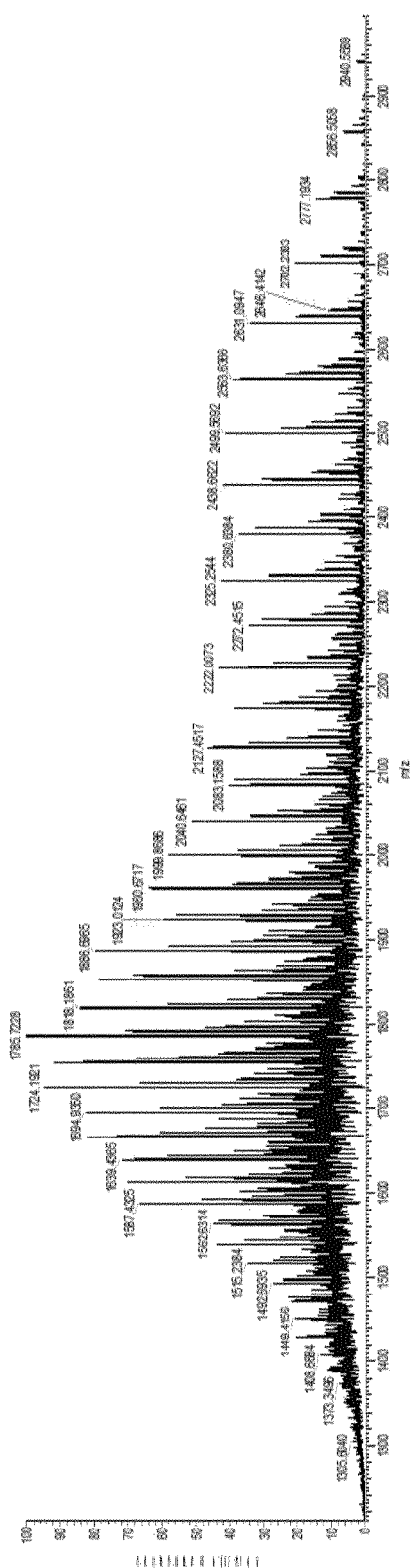
Figure 4B:
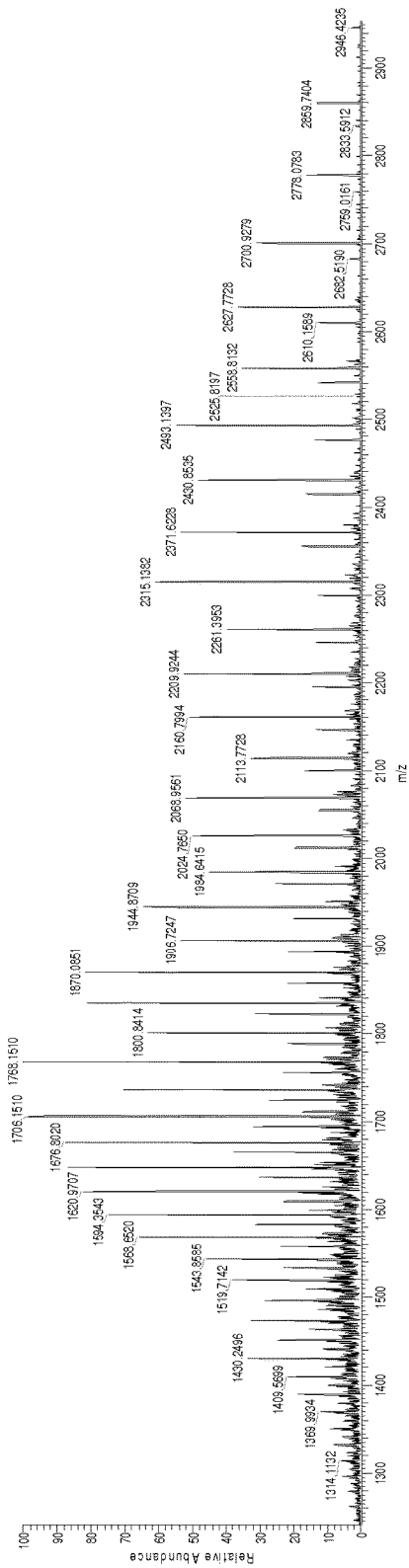
FIG. 4B shows the MS spectrum of the LC-MS analysis of Fab-Fab3b.

FIGS. 4A and 4B present the LC-MS analysis of Fab-Fab3a (containing a linker with SEQ ID NO: 6) and Fab-Fab3a (containing a linker with SEQ ID NO: 3), respectively. FIG. 4A demonstrates that the LC-MS spectrum of Fab-Fab3a with a linker corresponding to SEQ ID NO: 6 is significantly more heterogeneous than that of the related Fab-Fab3b antibody, which differed only in the composition of the linker (SEQ ID NO: 3). The linker sequence in the Fab-Fab3a antibody contains the PSTPPTPSPS (SEQ ID NO:22) sequence, which is found in the human IgA1 hinge and is known to be subject to O-linked glycosylation at 2 threonine and 2 serine residues. Since glycosylation of these sites is heterogeneous, the product usually possesses multiple glycoforms. whose populations are strongly affected by the expression conditions of the recombinant proteins. The total number of N-linked and O-linked glycosylation sites in Fab-Fab3a is at least 4, explaining the complex MS spectrum observed in FIG. 4A. The sequence of the linker corresponding to SEQ ID NO: 3 was designed in order to reduce heterogeneity due to non-homogeneous O-linked glycosylation. As such, several Serine and Threonine residues in the portion of the linker, whose sequence matched that of the sequence of the hinge of human IgA1 known to undergo O-linked glycosylation, were replaced with Glycine residues; additionally, several other Serine and Threonine residues were also replaced with Glycine in the linker. FIG. 4B shows that the MS spectrum of Fab-Fab3b containing the SEQ ID NO: 3 linker is substantially simplified; this is because the Fab-Fab3b analyte is less complex than the Fab-Fab3a analyte whose spectrum is presented in FIG. 4A. Thus, we concluded that the elimination of 4 O-linked glycosylation sites from the Fab-Fab3a antibody by replacing the linker of SEQ ID NO: 6 with the SEQ ID NO: 3 linker, resulted in a substantially more homogeneous BiXAb preparation.

Figure 5A:
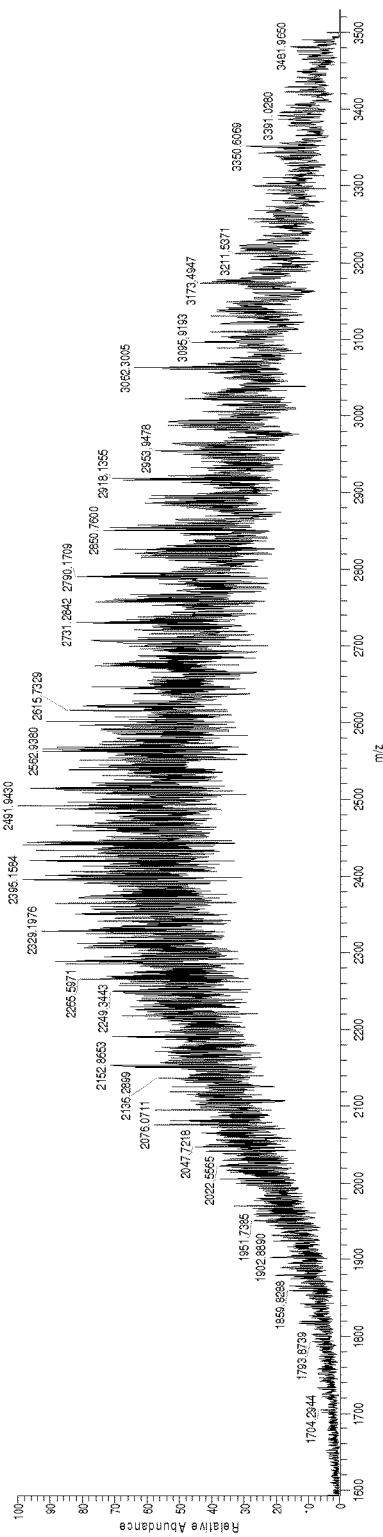
Figure 5B:
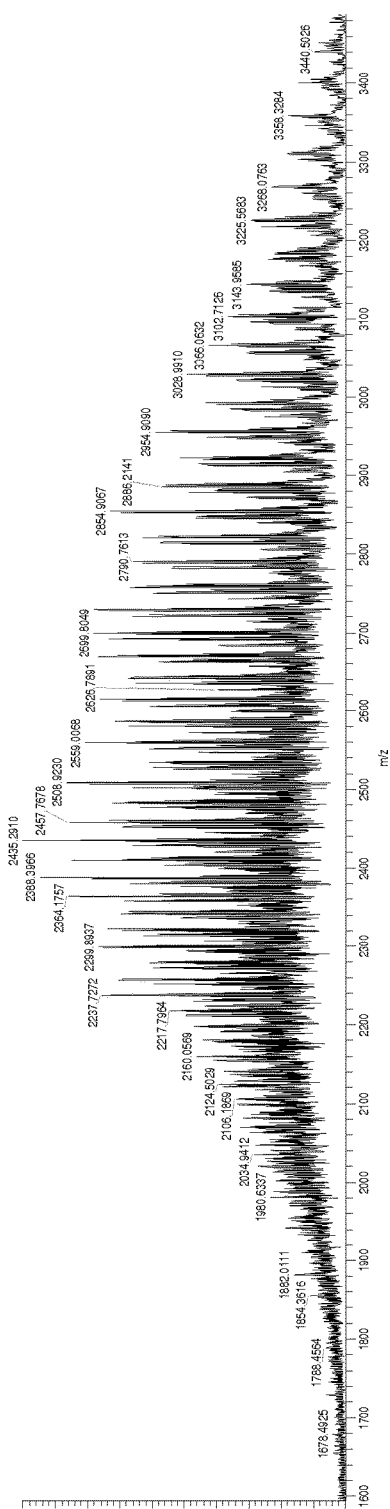
FIG. 5B shows the MS spectrum of the LC-MS analysis of BiXAb3b.

The difference in the homogeneity of bispecific antibodies containing SEQ ID NO: 6 and SEQ ID NO: 3 linkers was especially evident from the analysis of full-length BiXAb antibodies, which are symmetrical molecules that possess two linker sequences and thus possess an increased number of glycoforms in a BiXAb preparation. Additionally, BiXAbs possess two N-linked glycosylation sites, one on each Heavy Chain of the Fc-domain. The LC-MS spectra of BiXAb3a (constructed with the SEQ ID NO: 6 linker) and of BiXAb3b (constructed with the SEQ ID NO: 3 linker) are presented in FIGS. 5A and 5B, respectively. The BiXAb3a is expected to contain 8 additional O-linked glycosylation sites relative to the BiXAb3b, based on the differences in the linker sequences. The large number of O-linked glycosylation sites in BiXAb3a explains the highly complex MS spectrum in FIG. 5A. Both BiXAb antibodies possess 2 N-glycosylation sites in the Fc-domain resulting in additional glycoforms contributing to the heterogeneity of both BiXAbs, which explains the residual amount of heterogeneity in BiXAb3b observed in FIG. 5B.

The invention claimed is:

1. A multispecific antigen-binding fragment comprising at least two Fab fragments, wherein each Fab fragment recognizes a different epitope of interest, and said Fab fragments are tandemly arranged in any order, the C-terminal end of the CH1 domain of a first Fab fragment being linked to the N-terminal end of the VH domain of the following Fab fragment through a polypeptide linker, characterized in that the polypeptide linker sequence comprises
EPKX$_1$CDKX$_2$HX$_3$X$_4$PPX$_5$PAPELLGGPX$_6$X$_7$PPX$_8$PX$_9$PX$_{10}$GG (SEQ ID NO: 1),
wherein:
X$_1$, X$_2$ and X$_3$, identical or different, are Threonine (T) or Serine (S);
X$_4$ and X$_5$, identical or different, are any amino acid selected from the group consisting of Serine (S), Cysteine (C), Alanine (A), and Glycine (G); and
X$_6$, X$_7$, X$_8$, X$_9$, X$_{10}$, identical or different, are selected from the group consisting of Alanine (A), Glycine (G), Valine (V), Asparagine (N), Aspartic acid (D) and Isoleucine (I).

2. The multispecific antigen-binding fragment of claim 1, wherein:
a) X$_4$ is Serine (S) or Cysteine (C); or
b) X$_5$ is Alanine (A) or Cysteine (C).

3. The multispecific antigen-binding fragment of claim 2, wherein X$_6$, X$_7$, X$_8$, X$_9$, X$_{10}$, identical or different, are selected from the group consisting of Alanine (A) and Glycine (G).

4. The multispecific antigen-binding fragment of claim 3, wherein X$_6$ and X$_7$ are identical and are selected from the group consisting of Alanine (A) and Glycine (G).

5. The multispecific antigen-binding fragment of claim 3, wherein the polypeptide linker sequence comprises a sequence selected from the group consisting of:

```
                                          (SEQ ID NO: 3)
EPKSCDKTHTSPPAPAPELLGGPAAPPAPAPAGG;

(SEQ ID NO: 2)
EPKSCDKTHTSPPAPAPELLGGPGGPPGPGPGGG;
and (SEQ ID NO: 4)
EPKSCDKTHTSPPAPAPELLGGPAAPPGPAPGGG.
```

6. The multispecific antigen-binding fragment of claim 1, which recognizes both EGFR and HER2/neu.

7. The multispecific antigen-binding fragment of claim 1, which recognizes both CD38 and PD-L1.

8. The multispecific antigen-binding fragment of claim 1, said multispecific antigen-binding fragment comprising at least two Fab fragments with different CH1 and CL domains.

9. A multispecific antibody having two identical antigen-binding arms, each consisting of the multispecific antigen-binding fragment of claim 1.

10. The multispecific antibody of claim 9, which has an immunoglobulin-like structure, comprising:
two identical antigen-binding arms;
dimerized CH2 and CH3 domains of an immunoglobulin; and
a hinge region of an IgA, IgG, or IgD, linking the C-terminal ends of CH1 domains of the antigen-binding arms to the N-terminal ends of the CH2 domains.

11. A multispecific antibody comprising two heavy chains and four light chains,
wherein each heavy chain comprises:
a) a Fc region of an immunoglobulin comprising Hinge-CH2-CH3 domains;
b) wherein said Fc region is linked to Fab heavy chain CH1-VH of antibody 1 (Ab1) by said Hinge domain; and
c) wherein said Fab heavy chain CH1-VH of Ab1 is linked to Fab heavy chain CH1-VH of antibody 2 (Ab2) by a polypeptide linker sequence, wherein the polypeptide linker sequence links the N-terminus of said Fab heavy chain VH domain of Ab1 with the C-terminus of said Fab heavy chain CH1 domain of Ab2,
and the four light chains comprise light chains of Ab1 and light chains of Ab2 associated with their cognate heavy chain domains;
wherein the polypeptide linker sequence comprises EPKX$_1$CDKX$_2$HX$_3$X$_4$PPX$_5$PAPELLGGPX$_6$X$_7$PPX$_8$PX$_9$PX$_{10}$GG (SEQ ID NO: 1),
wherein:
X$_1$, X$_2$ and X$_3$, identical or different, are Threonine (T) or Serine (S);
X$_4$ and X$_5$, identical or different, are any amino acid selected from the group consisting of Serine (S), Cysteine (C), Alanine (A), and Glycine (G); and
X$_6$, X$_7$, X$_8$, X$_9$, X$_{10}$, identical or different, are selected from the group consisting of Alanine (A), Glycine (G), Valine (V), Asparagine (N), Aspartic acid (D) and Isoleucine (I).

12. The multispecific antibody of claim 11, wherein Ab1 and Ab2, being different, independently are selected from the group consisting of:
(i) cetuximab or a mutated derivative thereof, and
(ii) trastuzumab or a mutated derivative thereof.

* * * * *

UNITED STATES PATENT AND TRADEMARK OFFICE
CERTIFICATE OF CORRECTION

Page 1 of 1

PATENT NO. : 11,958,913 B2
APPLICATION NO. : 16/476624
DATED : April 16, 2024
INVENTOR(S) : Eugene Zhukovsky and Olivier Leger It is certified that error appears in the above-identified patent and that said Letters Patent is hereby corrected as shown below:

In the Specification

Column 1,
Line 66, "Fab 1" should read --Fab1--.

Column 2,
Line 20, "$X_8$, $X_0$, $X_{10}$" should read --$X_8$, $X_9$, $X_{10}$--.

Column 7,
Line 21, "Fab-Fab-Fc" should read --F(ab)'2-Fc--.

Column 12,
Line 57, "WIHwVRQ" should read --WIHWVRQ--.

Column 13,
Line 35, "SYLAVVYQQ" should read --SYLAWYQQ--.

Column 15,
Line 9, "KAPKWYSAS" should read --KAPKLLIYSAS--.
Line 64, "at 1-2×$10^6$/mL" should read --at 1~2×$10^6$/mL--.

Signed and Sealed this
Twenty-fifth Day of March, 2025

Coke Morgan Stewart
*Acting Director of the United States Patent and Trademark Office*